United States Patent
Saphier et al.

(10) Patent No.: US 11,590,164 B2
(45) Date of Patent: Feb. 28, 2023

(54) TOPICAL ANTIMICROBIAL FORMULATIONS CONTAINING MONOVALENT COPPER IONS AND SYSTEMS FOR GENERATING MONOVALENT COPPER IONS

(71) Applicants: Sami Shamoon College of Engineering (R.A.), Beer Sheva (IL); Oshra Saphier, Beer Sheva (IL); Yoram Shotland, Lehavim (IL); Stanislav Popov, Beer Sheva (IL); Magal Saphier, Beer Sheva (IL); Eldad Silberstein, Beer Sheva (IL)

(72) Inventors: Oshra Saphier, Beer Sheva (IL); Yoram Shotland, Lehavim (IL); Stanislav Popov, Beer Sheva (IL); Magal Saphier, Beer Sheva (IL); Eldad Silberstein, Beer Sheva (IL)

( * ) Notice: Subject to any disclaimer, the term of this patent is extended or adjusted under 35 U.S.C. 154(b) by 919 days.

(21) Appl. No.: 16/466,936

(22) PCT Filed: Dec. 5, 2017

(86) PCT No.: PCT/IL2017/051315
§ 371 (c)(1),
(2) Date: Jun. 5, 2019

(87) PCT Pub. No.: WO2018/104937
PCT Pub. Date: Jun. 14, 2018

(65) Prior Publication Data
US 2019/0350970 A1 Nov. 21, 2019

Related U.S. Application Data

(60) Provisional application No. 62/430,499, filed on Dec. 6, 2016.

(51) Int. Cl.
| | |
|---|---|
| *A61K 33/34* | (2006.01) |
| *A61K 8/19* | (2006.01) |
| *A61K 8/40* | (2006.01) |
| *A61K 8/67* | (2006.01) |
| *A61K 47/02* | (2006.01) |
| *A61K 47/10* | (2017.01) |
| *A61K 47/16* | (2006.01) |
| *A61K 47/20* | (2006.01) |
| *A61K 47/22* | (2006.01) |
| *A61K 47/44* | (2017.01) |
| *A61L 15/18* | (2006.01) |
| *A61L 15/44* | (2006.01) |
| *A61L 15/58* | (2006.01) |
| *A61Q 17/00* | (2006.01) |

(52) U.S. Cl.
CPC ............. *A61K 33/34* (2013.01); *A61K 8/19* (2013.01); *A61K 8/40* (2013.01); *A61K 8/676* (2013.01); *A61K 47/02* (2013.01); *A61K 47/10* (2013.01); *A61K 47/16* (2013.01); *A61K 47/20* (2013.01); *A61K 47/22* (2013.01); *A61K 47/44* (2013.01); *A61L 15/18* (2013.01); *A61L 15/44* (2013.01); *A61L 15/58* (2013.01); *A61Q 17/005* (2013.01); *A61K 2800/58* (2013.01); *A61L 2300/102* (2013.01); *A61L 2300/404* (2013.01); *A61L 2300/802* (2013.01)

(58) Field of Classification Search
CPC ............ A61K 33/34; A61K 8/19; A61K 8/40; A61K 8/676; A61K 47/02; A61K 47/10; A61K 47/16; A61K 47/20; A61K 47/22; A61K 47/44; A61K 2800/58; A61K 31/365; A61K 8/365; A61L 15/18; A61L 15/44; A61L 15/58; A61L 2300/102; A61L 2300/404; A61L 2300/802; A61L 15/46; A61Q 17/005; A61P 17/02
See application file for complete search history.

(56) References Cited

U.S. PATENT DOCUMENTS

| | | | |
|---|---|---|---|
| 4,797,274 A * | 1/1989 | Miki | A01N 59/20 424/76.1 |
| 5,458,906 A | 10/1995 | Liang | |
| 2008/0311165 A1 | 12/2008 | Gabbay | |
| 2014/0271757 A1 | 9/2014 | Agrawal et al. | |
| 2014/0296155 A1 | 10/2014 | Newburger et al. | |
| 2016/0220728 A1 | 8/2016 | Adams | |

OTHER PUBLICATIONS

Golub, Gilad, et al. The Stabilization of Monovalent Copper Ions by Complexation with Saturated Tertiary Amine Ligands in Aqueous Solutions. The Case of 2,5,9,12-Tetramethyl-2,5,9,12-tetraazatridecane, J. Chem. Soc., Chem. Communications, Issue 5, p. 397-398, Dec. 31, 1992 (Jan. 1, 1992).
Zimmerman, Leonard, Toxicity of Copper and Ascorbic Acide to Serratia marcescens, Journal of Bacteriology, Am. Soc. of Microbiology, vol. 91, No. 4, p. 1537-1542, Apr. 30, 1966.
PCT/IL2017/051315 International Search Report dated Feb. 25, 2018.
Michael B. Davies et al., "The Reaction between Copper(II) Ions and L-Ascorbic Acid in Chloride Media", Inorganica Chimica Acta, 146 (1988) 59-63.
Apr. 11, 2022 Office Action issued in corresponding European Patent Application No. 17877956.7.

* cited by examiner

*Primary Examiner* — Robert A Wax
*Assistant Examiner* — Quanglong N Truong
(74) *Attorney, Agent, or Firm* — Honigman LLP; Brett A. Krueger

(57) ABSTRACT

The present invention relates to antimicrobial formulations. More particularly, the invention relates to monovalent copper-containing and/or monovalent copper-generating products for healing wounds and burns, and particularly for chronic wounds, prevention of wound infections and infections in various implants as well as medical/surgical devices.

12 Claims, 10 Drawing Sheets

TOPICAL ANTIMICROBIAL FORMULATIONS CONTAINING MONOVALENT COPPER IONS AND SYSTEMS FOR GENERATING MONOVALENT COPPER IONS

CROSS-REFERENCE TO RELATED APPLICATIONS

This application is a National Stage Application and claims priority under 35 U.S.C. § 371 to Patent Cooperation Treaty application PCT/IL2017/051315, filed Dec. 5, 2017, which claims the benefit of U.S. Provisional Application No. 62/430,499, filed Dec. 6, 2016. Priority is claimed to both of these applications and the disclosures of these prior applications are considered part of the disclosure of this application, and to the extent allowed, the entire contents of the aforementioned applications are incorporated herein.

FIELD OF THE INVENTION

The present invention relates to antimicrobial formulations. More particularly, the invention relates to monovalent copper-containing and/or monovalent copper-generating products for healing wounds and burns, and particularly for chronic wounds, prevention of wound infections and infections in various implants as well as medical/surgical devices.

BACKGROUND OF THE INVENTION

Copper (Cu) is an essential trace element for most living organisms. However, in high concentration it can exert biocidal effect in various mechanisms, most of them are yet not fully understood (Grass Get al., Appl. Environ. Microbiol., 2011; 77(5):1541-1547). First mentioned in an Egyptian papyrus dated back to 2600-2200 BC, the antimicrobial properties of copper have been well recognized and documented throughout history (Dollwet H. et al., Trace Elements Med. 1985; 2(2):80-87).

Over recent decades, copper has regained scientific interest due to its possible applications in the healthcare setting. One of the most common and established medical applications of copper is the addition of ionized copper-silver in hospital water systems as an effective method to control Hospital-acquired Legionella infection (Stout J. E. et al., Infect. Control Hosp. Epidemiol., 2003; 24(8):563-568). Various studies have demonstrated the effective impact of copper biocidal surfaces in reducing the spread of various bacteria, yeasts and viruses, a conclusion that was later on supported in clinical trials.

The mechanisms behind copper toxicity are still a subject of ongoing research, but a number of contributing factors have already been established. A major factor is the ability to act as a catalyst for oxidative damage to tissues through cyclic redox reactions, alternating between Cu(I) and Cu(II). The reactive oxygen species generated in these reactions directly damage essential cell components like nucleic acids, proteins, and lipids. Intracellular free copper ions also contribute to cell death through protein inactivation. The significance of the effect of copper on DNA degradation is still controversial, with different mechanisms of toxicity observed in different types of microorganisms. In several studies that involved enterococci DNA degradation as a result of copper ionic species and the generation of superoxides was a key factor in cell death process (Warnes S L et al., Appl. Environ. Microbiol., 2010 August; 76(16): 5390-401; Warnes S L et al., Appl. Environ. Microbiol., 2011 September; 77 (17): 6049-6059). In contrast, other studies that explored copper toxic effects on Gram-negative bacteria such as *Escherichia coli* and yeasts suggested that depolarization of the cytoplasmic membrane is the main target, while DNA degradation occurs only after cell death (Macomber L. et al., J. Bacteriol. 2007, March; 189(5):1616-26; Quaranta D. et al., Appl. Environ. Microbiol., 2011, January; 77(2):416-26).

The two most common ions formed by copper are the +1 (cuprous) and +2 (cupric) ions. The cuprous ion is the chemically more active and less stable of the two oxidation states, and is easily oxidized in an aqueous environment. However, it is possible to maintain high concentration of cuprous ions in aqueous environment by adding reagents which form a very stable complex with the cuprous ion, such as acetonitrile ($CH_3CN$) (Parker A. J. et al., Journal of Solution Chemistry, November 1981, Volume 10, Issue 11, pp 757-774) or benzoic acid ($C_6H_5COOH$) (Saphier M. et al., J. Chem. Soc., Dalton Ttans., 1845-1849, 1999). Keeping the environment anaerobic also helps in stabilizing the cuprous form.

Currently, Ag (I) (Silver) ions are used to treat wound infection in burn victims as well as in chronic wounds. The present invention demonstrates that the use of Cu (I) ions, rather than Ag (I) ions or Cu (II) and metallic copper, is more efficient in eliminating Bacteria (such as *Escherichia coli*, *Staphylococcus aureus*) and yeast (such as *Saccharomyces cerevisiae*).

SUMMARY OF THE INVENTION

The present invention relates to antimicrobial formulations comprising cuprous (monovalent copper ion, $Cu^{1+}$) or cuprous generating systems as the antimicrobial agent for use as dressings for healing of wounds and burns and particularly chronic wounds, prevention of wound infections and infections in various implants as well as medical/surgical devices.

One embodiment of the present invention relates to antimicrobial formulations comprising monovalent copper ions (cuprous, $Cu^{1+}$.

Another embodiment of the present invention relates to the antimicrobial formulation as described above, wherein the monovalent copper is produced in situ by reduction of divalent copper (cupric, $Cu^{2+}$) salts in the present of a reducing agent.

A further embodiment of the present invention relates to the antimicrobial formulation as described above, wherein the monovalent copper is produced in situ by reduction of divalent copper (cupric, $Cu^{2+}$) salts in the presence of metallic copper and stabilizing ligands.

In another embodiment of the present invention, the metallic copper is in the form of powder, wires, net, sheets or nano-particles.

In a specific embodiment of the present invention, the stabilizing ligand is acetonitrile.

In a specific embodiment of the present invention, the reducing agent is ascorbic acid or derivatives or salts thereof.

One embodiment of the present invention provides an antimicrobial formulation comprising:

ointment comprising copper powder as a metallic copper source, copper(II) gluconate as a divalent copper ions source, ascorbyl palmitate as a reducing agent, and glycerol, vaseline, lanolin and water as filling agents.

In another embodiment, the present invention provides an antimicrobial formulation comprising:

ointment comprising copper powder as a metallic copper source, copper(II) gluconate as a divalent copper ions source, ascorbyl palmitate as a reducing agent, and water, stearyl alcohol, sodium lauryl sulfate, glycerol and vaseline as filling agents.

In a further embodiment of the present invention there is provided the antimicrobial formulation as described above for use as dressings for healing of chronic wounds and burns.

In a yet another embodiment, the present invention provides the antimicrobial formulation as described above for use in preventing wound infections.

Another embodiment of the present invention relates to the antimicrobial formulation as described above for use in preventing infections in implants and medical/surgical devices.

A further embodiment of the present invention provides a composition comprising the antimicrobial formulation as described above for use as a cosmetic composition for skin healing.

A further embodiment of the present invention provides a cosmetic composition comprising the antimicrobial formulation as described above for use in the treatment of skin infections, such as acne and herpes.

A further embodiment of the present invention provides a bandage comprising the formulation as described above for use in the treatment of anaerobic infections.

A specific embodiment of the present invention provides a bandage as described above, wherein the external side of the bandage is sealed against penetration of oxygen from the external environment.

Another embodiment of the present invention provides an adhesive bandage comprising:
  copper wires; and
  ointment comprising divalent copper ions source, a reducing agent, a filling agent and glycerol.

DETAILED DESCRIPTION

Figure 1:
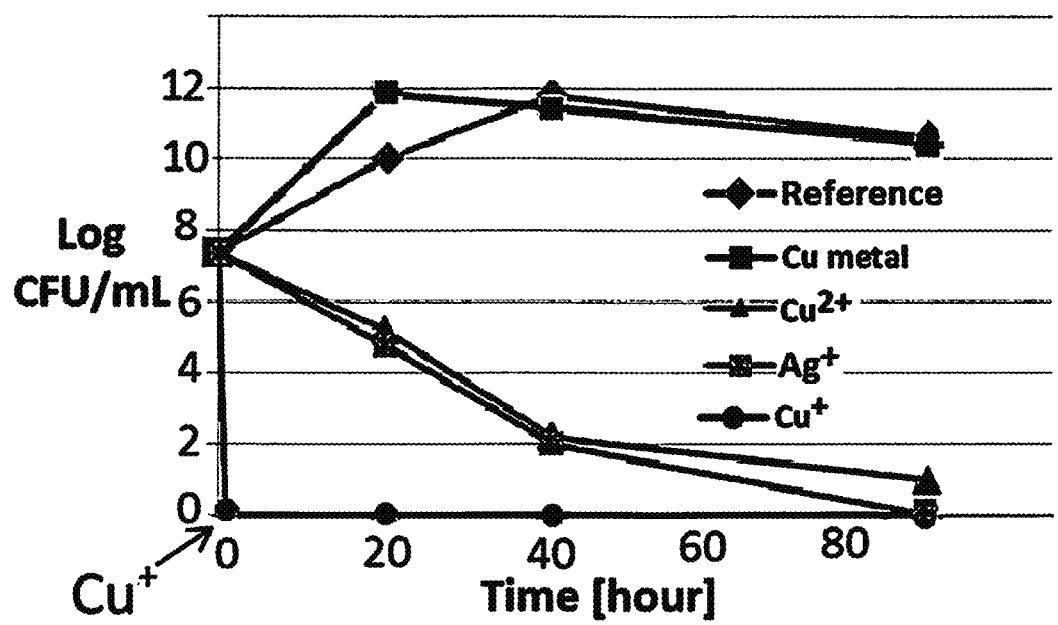
FIG. 1 shows the viable cell count of *E. coli* bacteria (Δ log cfu/ml) over time of treating with $Cu^{1+}$, $Cu^{2+}$, $Ag^{1+}$ and control groups (no copper and metal copper alone), using syringes technique.

The present invention exemplifies the potency of $Cu^{1+}$ over $Cu^{2+}$ copper ion in eliminating various microorganisms. $Cu^{1+}$ was found to be more potent antimicrobial agent than $Ag^+$, which is a popular antimicrobial ion used in many modern types of wound dressings. Therefore, the present invention provides a more potent antimicrobial dressings comprising $Cu^{1+}$ as an active agent. The results of this study are consistent when using two different methods of bacterial growth and, more importantly, when using two different chemical reactions for the in situ production of $Cu^{1+}$— one with metallic copper and acetonitrile and the other with ascorbic acid. Both materials are non-toxic agents.

Definitions

The term "microbial" refers herein to any kind of bacteria, yeast, fungus and virus.

The term "metallic copper" refers herein to copper in its metallic form, namely, oxidation state 0. The metallic copper may be, but not limited to, in the form of powder, wires, net, sheets, nano particles or any other known form.

The term "stabilizing ligand" refers herein to a non-toxic ligand which is able to stabilize monovalent copper ions. Such a ligand might be acetonitrile, organic compounds comprising double bonds, aromatic rings, tertiary amines or multi-dentate ligands, such as fumaric acid, maleic acid, beta-carotene, salicylic acid, benzoic acid, acetylsalicylic acid, 2,5,9,12-tetramethyl-2,5,9,12-tetraazatridecane. A preferred ligand is acetonitrile.

The term "reducing agent" refers herein to a non-toxic agent which is able to reduce divalent copper ions into monovalent copper ions. Such an agent might be metals, such as aluminum, iron and copper, and biological reducing agents (antioxidants) such as ascorbic acid, beta-carotene and folic acid. A preferred reducing agent is ascorbyl palmitate or metallic copper as copper powder.

The term "divalent copper ions source" refers herein to a non-toxic compound, salt or complex which is able to release divalent copper ions into the reaction mixture. Such a source might be $CuSO_4$, $CuCl_2$, $CuCO_3$, $Cu_3(PO_4)_2$, $Cu(CH_3COO)_2$, $Cu(C_6H_5CO_2)_2$, or $CuO$. A preferred divalent copper ions source is $CuSO_4$ or copper(II) D-gluconate.

The term "filling agent" refers herein to a structural agent such as used in the cosmetics and in medical formulations. Examples of such an agent are poly(vinyl alcohol) (PVA), stearyl alcohol, sodium lauryl sulfate, glycerol, lanolin, Vaseline or combinations thereof.

The term "emollient" refers herein to supple, waxlike, lubricating, thickening agent that prevents water loss and has a softening and soothing effect on skin. Examples of emollients are ingredients like plant oils, mineral oil, petrolatum, and fatty acids. More specifically, emollient may refer to Vaseline, lanolin, triglycerides, benzoates, myristates, palmitates, and stearates.

The term "vehicle" refers herein to any carrier or inert medium used as a solvent (or diluent) in which the medicinally active agent is formulated and or administered.

Three groups of filling agents are possible:
1. Cream (Example 1)—emulsion of water (e.g., 60-80% buffer (0.1M PBS), oil (20-40% oil component, e.g., mineral or vegetable oil) and emulsifier 2% (e.g. carboxymethyl cellulose, lanolin)
2. Ointment (Example 2)—semi-solid preparations of hydrocarbons (petrolatum, mineral oil, paraffin, synthetic hydrocarbons)
3. Paste—mixture of powder and ointment (e.g., zinc oxide 20% paste)
4.

All possible groups have to contain copper source, reducing agent and/or stabilizing ligand.

Materials and Methods

Syringes technique: Bacteria cells were incubated at room temperature under anaerobic conditions in LB Bruce growth substance syringes. To ensure anaerobic conditions, Argon gas (UHP) was bubbled through a sterile filter into a syringe filled with a growth substance. $Cu^{1+}$ was formed in situ, the process was started with de-aerating the aqueous solutions containing a mixture of $CuSO_4$ as the source for $Cu^{2+}$ ions, metallic copper and Acetonitrile as a stabilizing ligand, prior to microorganisms insertion, according to the following reaction:

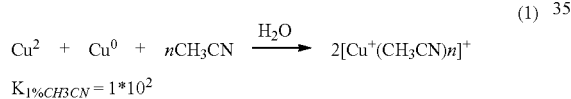

$$Cu^2 + Cu^0 + nCH_3CN \xrightarrow{H_2O} 2[Cu^+(CH_3CN)n]^+ \quad (1)$$

$K_{1\%CH3CN} = 1*10^2$

One must notice that each $Cu^{2+}$ results in two $Cu^{1+}$ ions.

0.1 M acetonitrile (0.5% V/V), which according to preliminary tests was shown to be the minimal effective concentration, was use as a stabilizing ligand.

Reference bacteria were incubated under the same condition in a growth substance containing: Metallic copper (4×2×0.1 cm), Acetonitrile, $CuSO_4$ or $AgNO_3$.

Bacteria count was measured at time intervals using a series of dilutions, and colonies count on LB Agar was incubated at 37° C.

Petri dish technique: Bacteria were incubated at 37° C. in Petri dish with LB Agar containing 20 mM ascorbic acid and 0.05-3.5 mM $CuSO_4$ covered by oil, to prevent air oxygen penetration. As control groups, bacteria were incubated under the same conditions without ascorbic acid, or without $CuSO_4$. In this series of experiments ascorbic acid acted as the reducing agent according to the following reaction:

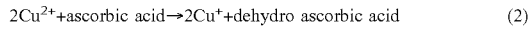

$$2Cu^{2+} + \text{ascorbic acid} \rightarrow 2Cu^+ + \text{dehydro ascorbic acid} \quad (2)$$

The viability of bacteria was detected by the presence or absence of colonies.

Disc Diffusion Antibiotic Sensitivity Test:
1. Introduction:
The antibacterial effect was measured by an agar disk diffusion method. *Escherichia coli* strain MG1655 was used as a model organism. Whatman's 6 mm disks were used. The incubation of Petri dishes (with disks) was done in aerobic conditions, at 37° C. After 24 h incubation, the radiuses of sterile zones on agar were measured.

2. Experimental procedure:
2.1 Preparation of bacterial suspension

100 μl of bacterial suspension (containing $10^4$-$10^5$ bacterial cells per plate) was used for testing. Cells of *E. coli* MG1655 were grown overnight as a starter on LB (Luria broth) media at 37° C. with a shaker. After 12-18 hhours incubation, 100 μL suspension were added to 9.9 mL of fresh LB media. Bacterial cells designated for testing were grown in fresh LB at 37° C. with a shaker for 2-3 h to final OD (600 nm) 0.2-0.4. This cell suspension was diluted by a factor of 100 using 0.9% NaCl, and 100 μL of the diluted suspension was distributed on agar surface before adding a disk.

2.2 Preparation of Petri dishes

LB agar was prepared according to a standard procedure, autoclaved and stored afterwards up to 3 h at 55° C. The needed substances (like ascorbic acid) were added into agar before pouring into dishes. 15 ml agar was added to each 90 mm Petri dish. Dishes were dried for at least 1 h in a biosafety cabinet by sterile air flow.

2.3 Formulation application

To the preliminary dried dishes (a described in 2.2) a freshly prepared bacterial culture was added (as described in 2.1). Immediately after absorption of the suspension into the agar, a disk was placed at the center of the dish. In case where metallic copper was tested, it was placed first in the form of a small circular wire at the dish center and pressed into the agar, and covered by a disk afterwards. 10 μl of a $Cu^{2+}$ solution was placed on the disk.

2.4 Measurement of the sterile zone size

All dishes after 24 h incubation (as described in 2.1) were photographed and the images are analyzed. The absolute size of the sterile zones was estimated in comparison with the disk size (6 mm).

The results were presented as sterile area in $mm^2$ (FIG. 5 and Table 2) or as radiuses in mm (FIGS. 7-10) of the sterile zones on agar.

Results

The vitality of *Escherichia coli, Staphylococcus aureus* (bacteria) and *Saccharomyces cerevisiae* (yeast) was tested in anaerobic conditions using syringe technique and Petri dish technique.

The following four different conditions were tested:

A—a syringe containing metallic copper with Cu' reacting in the presence of $CH_3CN$ to give 2 $Cu^{1+}$ prior to bacteria insertion;

B— a syringe containing $Cu^{2+}$ only;

C— a syringe containing metallic copper; and

D—a reference syringe without copper.

The Effect of $Cu^{1+}$, $Cu^{2+}$, $Cu^0$ on Gram Negative Bacteria (*E. coli*)

Table 1 summarizes 16 various experiments with different concentrations of $Cu^{1+}$, $Cu^{2+}$, and control groups (no copper and metal copper alone). $Cu^{1+}$ is stable only under the conditions presented in column A.

TABLE 1

| Initial concentration $CuSO_4$ mM | $CH_3CN$ % v/v | (A) $CuSO_4$ and Metal copper ($Cu^{1+}$) | (B) Only $CuSO_4$ ($Cu^{2+}$) | (C) Only Metal copper | (D) No Copper |
|---|---|---|---|---|---|
| 4.0 | 0.25 | + | + | + | + |
| 4.0 | 0.5 | − | + | + | + |
| 0.4 | 0.5 | − | + | + | + |
| 0.3 | 0.5 | + | + | + | + |

Table 2 compares the antibacterial efficacy of $Cu^{1+}$ with $Ag^{1+}$ and $Cu^{2+}$, tested on E. coli by disk diffusion method. It is shown that exposure to $Cu^{1+}$ provides more than 10 times improvement in the biocidal effect.

TABLE 2

| Ion | Estimate of the sterile area beyond the disk (mm$^2$) |
|---|---|
| $Cu^{1+}$ | 359.3 |
| $Ag^{1+}$ | 27.1 |
| $Cu^{2+}$ | 25.9 |

Minimal Inhibitory Concentration (MIC) of Univalent and Divalent Copper Ions on E. coli.

The MIC of $Cu^{1+}$ and $Cu^{2+}$ was measured by using four syringes with decreasing concentration of the copper ions from 8 to 2 mM.

TABLE 3

| $Cu^{1+}$ 2 mM | $Cu^{1+}$ 4 mM | $Cu^{1+}$ 6 mM | $Cu^{1+}$ 8 mM | $Cu^{+2}$ 2 mM | $Cu^{+2}$ 4 mM | $Cu^{+2}$ 6 mM | $Cu^{2+}$ 8 mM | positive control without copper | negative control without E. coli |
|---|---|---|---|---|---|---|---|---|---|
| ++ | 107 | − | − | ++ | ++ | + | − | ++ | − |

Table 3 shows the presence ("++" represents a fully covered plate, estimated as 2×10$^7$ cfu/ml; "+" represents partially covered plate but still uncountable, estimated as 1×10$^4$ cfu/ml; when a number is given, it indicates the number of colonies on the plate) or absence (−) of E. coli colonies after 24 h incubation with decreasing concentrations of copper ions and 0.5% (v/v) of acetonitrile. MIC of $Cu^{1+}$ found to be around 4 mM where the MIC of $Cu^{2+}$ was between 6 mM and 8 mM.

Petri Dish Technique:

The experiment was repeated using a different reducing agent (ascorbic acid instead of metal copper with acetonitrile) and different technique of growing bacteria on Petri dishes with LB agar. The ascorbic acid embedded in the agar reduces copper as was shown in Equation 2.

TABLE 4

| Ascorbic acid | 20 mM | 20 mM | 20 mM | 0 mM | 0 mM |
|---|---|---|---|---|---|
| $CuSO_4$ | 0 mM | 0.01 mM | 0.05 mM | 3.0 mM | 4.0 mM |
| Vitality of E. coli MG 1655 | ++ | ++ | − | ++ | − |

Table 4 demonstrates the ascorbic acid and copper ion concentration effect on E. coli vitality 24 h after incubation. The bactericidal effect of reduced copper ions ($Cu^{1+}$) was eight times higher than that of $Cu^{2+}$.

Kinetics of Bactericidal Effect of Copper and Silver Ions on E. coli

Because of the chemical similarity of copper and silver as well as their clinical use as antibacterial agents, their antibacterial effect over time was compared. The survival of test bacteria in each syringe was sampled in time intervals of 1, 20, 40 and 85 hours from inoculation. Time-kill curve was constructed by plotting the viable cell count of bacteria (Δ log 10 cfu/ml) over time (FIG. 1).

The syringe with $Cu^{1+}$ ions demonstrated a significant reduction of the initial bacteria inoculums by 7 log cfu/ml after 1 h of incubation in anaerobic environment. In the next sample, 20 hours after inoculation, no viable bacteria cell was found at all. A more gradual decline in the viable cell count along time was observed in the $Cu^{+2}$ syringe, and it should be noted that even after 85 hours, live bacteria still remained in the syringe (1 log cfu/ml). A similar pattern of decline was seen in the syringe that contained silver ions ($Ag^+$), but after 85 hours no viable cells were found. As expected, none of the negative control syringes showed toxic effect on bacteria survival during the experiment timeline.

Figure 2:
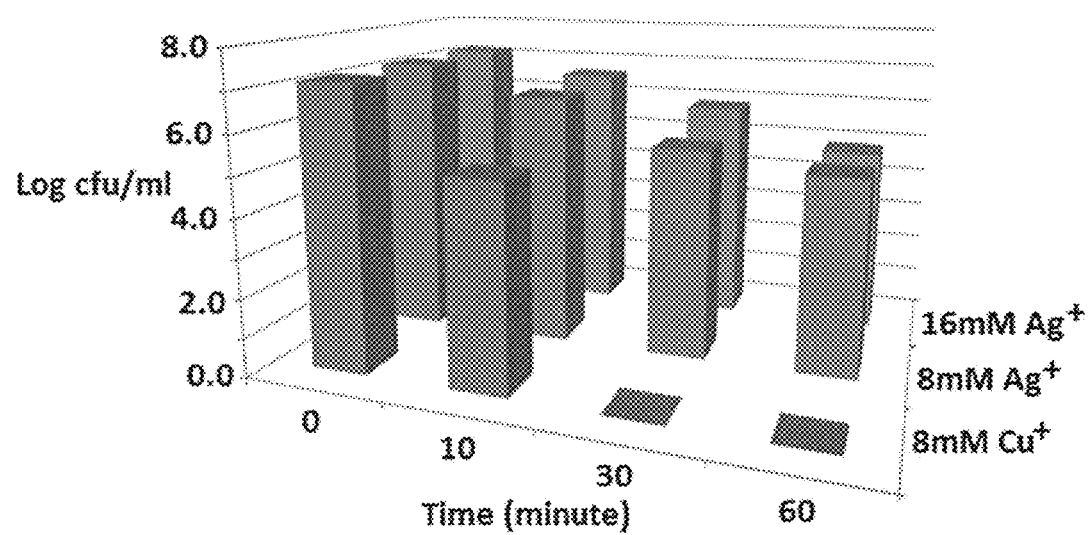
FIG. 2 shows the viable cell count of *E. coli* bacteria (Δ log cfu/ml) over time of treating with $Cu^{1+}$, 8 mM $Ag^{1+}$ and 16 mM $Ag^{1+}$, using syringes technique.

FIG. 2 shows the result of 1 h incubation of E. coli with 8 mM $Cu^{1+}$ compared to 8 mM and 16 mM of $Ag^+$. That experiment demonstrates that even when doubling the $Ag^+$ concentration $Cu^{1+}$ is a more potent antibacterial agent.

The Effect $Cu_{1+}$, $Cu_{1+}$, $Cu^0$ on Gram Positive Bacteria (Staphylococcus aureus)

The MIC of $Cu^{1+}$ is measured by using Petri dishes with LB agar. The ascorbic acid embedded in the agar reduces copper as was shown in Equation 2.

TABLE 5

| Control without S. aureus | Control without copper(I) and ascorbic acid | Copper(I) 0.3 mM with Ascorbic acid 20 mM | Copper(I) 0.1 mM with Ascorbic acid 20 mM | Copper(I) 0.05 mM with Ascorbic acid 20 mM |
|---|---|---|---|---|
| − | ++ | − | 45 | ++ |

Table 5 demonstrates the ascorbic acid and copper ion concentration effect on S. aureus vitality 24 h after incubation.

Figure 3:
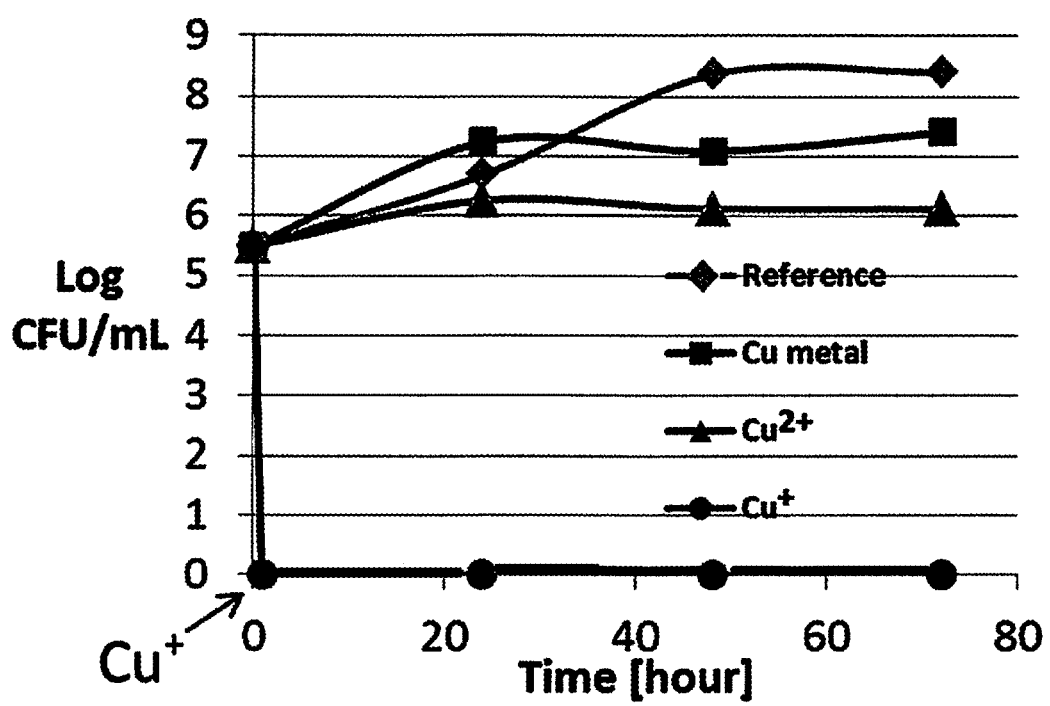
FIG. 3 shows the viable cell count of *Staphylococcus aureus* bacteria (Δ log cfu/ml) over time of treating with $Cu^{1+}$, $Cu^{2+}$ and control groups (no copper and metal copper alone), using syringes technique.

FIG. 3 demonstrates the growth kinetics of gram positive Staphylococcus aureus in anaerobic conditions using the syringe technique in the presence of $Cu^{1+}$, $Cu^{2+}$, metallic Cu and control. It is noticeable that $Cu^{2+}$ had very little bacteriostatic effect while exposure to $Cu_{1+}$ caused depletion of bacterial count within 1 h of incubation. When comparing with FIG. 2 it seems that the difference between the effect of $Cu^{1+}$ and $Cu^{2+}$ is more pronounced in gram (+) bacteria than in gram(−).

The Effect $Cu^{1+}$, $Cu^{2+}$, $Cu^0$ on Gram Positive Yeast (Saccharomyces cerevisiae)

Figure 4:
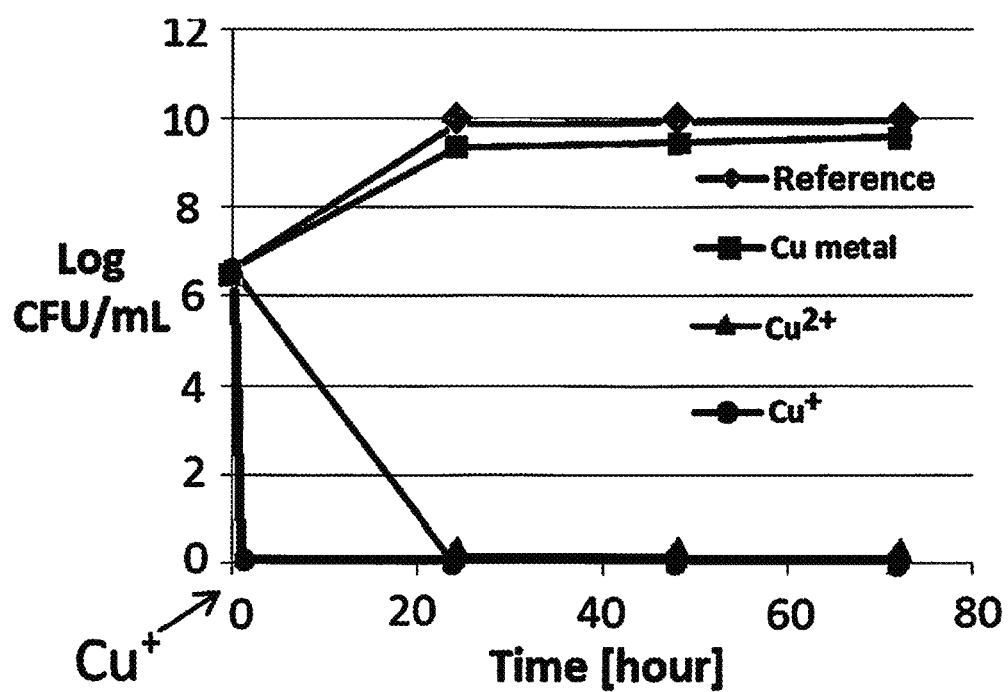
FIG. 4 shows the viable cell count of *Saccharomyces cerevisiae* yeast (Δ log cfu/ml) over time of treating with $Cu^{1+}$, $Cu^{2+}$ and control groups (no copper and metal copper alone), using syringes technique.

Similar effect is found with Saccharomyces cerevisiae (FIG. 4), however, the yeasts were more susceptible to $Cu^{2+}$ than both bacteria studied.

Disc Diffusion Antibiotic Sensitivity Test

Figure 5:
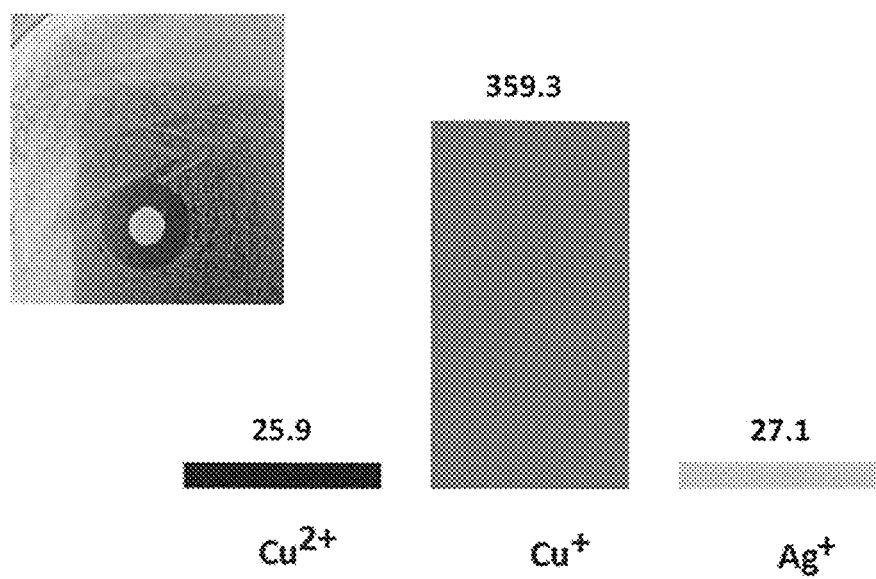
FIG. 5 shows the results of a disc diffusion antibiotic sensitivity test (as radiuses in mm of sterile zones on agar), exemplifying the advantage of the $Cu^{1+}$ ions over $Ag^{1+}$ and $Cu^{2+}$.

The results of the disc diffusion antibiotic sensitivity test are presented in FIG. 5. $Cu^{1+}$ yields a sterile area of 359.3 mm², much larger than the area resulted from the Ag⁺ disc (27.1 mm²) and the $Cu^{+2}$ disc (25.9 mm²). The results are another indication for the superiority of the monovalent copper ions as an antimicrobial agent in comparison with the traditional silver ions and divalent copper ions.

Use of $Cu^{1+}$ as an Antimicrobial Dressing

The improved antimicrobial effect of monovalent copper ions, especially under anaerobic conditions, is demonstrated above. Anaerobic bacteria play a major role in the pathogenesis of chronic ulcers as well as major burns. Therefore, monovalent coppers ions can be used as an active agent in topical antimicrobial formulations.

One embodiment of the invention relates to an adhesive bandage comprising:
copper wires; and
ointment comprising divalent copper ions source, reducing agent, filling and glycerol.

Figure 6:
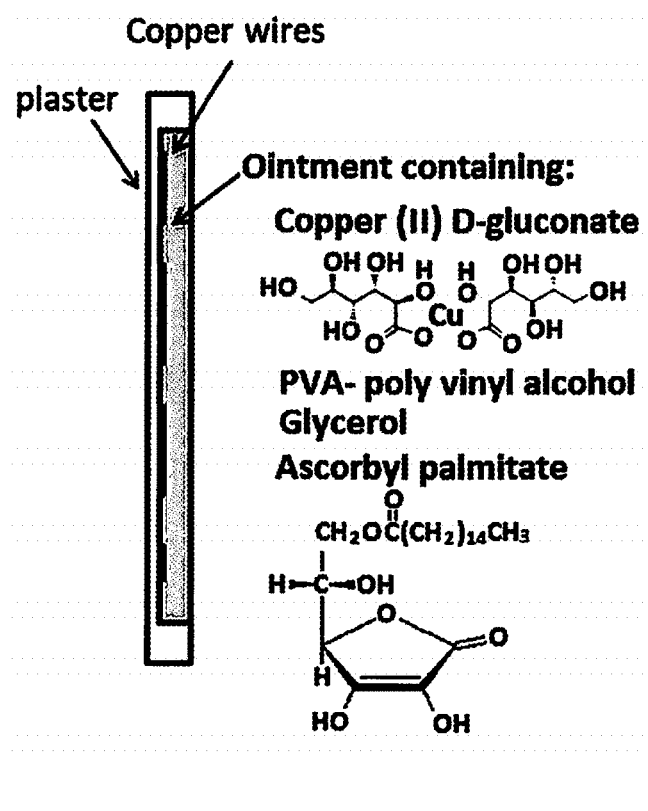
FIG. 6 shows a schematic representation of the structure of an adhesive bandage comprising the cuprous ions as an antimicrobial agent for improved healing for chronic non-healing wounds and burns.

A Schematic example of such an adhesive bandage is presented in FIG. 6.

This invention has further the potential to be impregnated into surgical sutures and into medical/surgical implants and devices and reduce the rate of implant/device related infections. It further has the potential to reduce the formation of biofilm around implants thus enabling other antibiotics to reach the implant site in case of infection, as well as reducing the chance of other biofilm related morbidity such as capsular contracture.

EXAMPLES

Example 1—Emulsifying Base Ointments that Generate Cu(I) Ions

Preparation

The ointment having in situ Cu(I) generating mechanism was made by mixing of ointment base (emollient and vehicle) with copper(II) gluconate, ascorbyl palmitate and copper powder. The mixing can be done with mortar and pestle for massive quantities (20-100 g) of ointment, and with the help of a clock glass and plastic spatula for a small amount (1-4 g) of ointment. The proportion of copper(II) gluconate and ascorbyl palmitate was used as for absorption ointment (1.4:1), as described in Example 2 below, and 2% w.t. of copper in the powder form was added to each sample. The following ointments with different mass concentrations of copper(II) gluconate were made: 0.625% w.t. (E-0), 1.25% w.t. (E-1), 2.5% w.t. (E-2), 5% w.t. (E-10) and 15% w.t. (see Table 6).

TABLE 6

Composition of emulsifying base ointments that generate Cu(I) ions

| Component | Ointment Amount (% w.t.) | | | | | |
|---|---|---|---|---|---|---|
| | E-0 | E-1 | E-2 | E-5 | E-10 | E-15 |
| Water | 35.88 | 35.50 | 34.73 | 33.21 | 30.16 | 27.10 |
| Stearyl alcohol | 24.24 | 23.98 | 23.47 | 22.44 | 20.38 | 18.31 |
| Vaseline | 24.24 | 23.98 | 23.47 | 22.44 | 20.38 | 18.31 |
| Glycerol | 11.64 | 11.51 | 11.27 | 10.77 | 9.78 | 8.79 |
| Sodium lauryl sulfate | 0.97 | 0.96 | 0.94 | 0.90 | 0.82 | 0.73 |
| Copper(II) gluconate | 0.63 | 1.25 | 2.50 | 5.00 | 10.00 | 15.00 |
| Ascorbyl palmitate | 0.41 | 0.81 | 1.63 | 3.25 | 6.50 | 9.75 |
| Copper powder | 2.00 | 2.00 | 2.00 | 2.00 | 2.00 | 2.00 |

Antibacterial Effect

Figure 7:
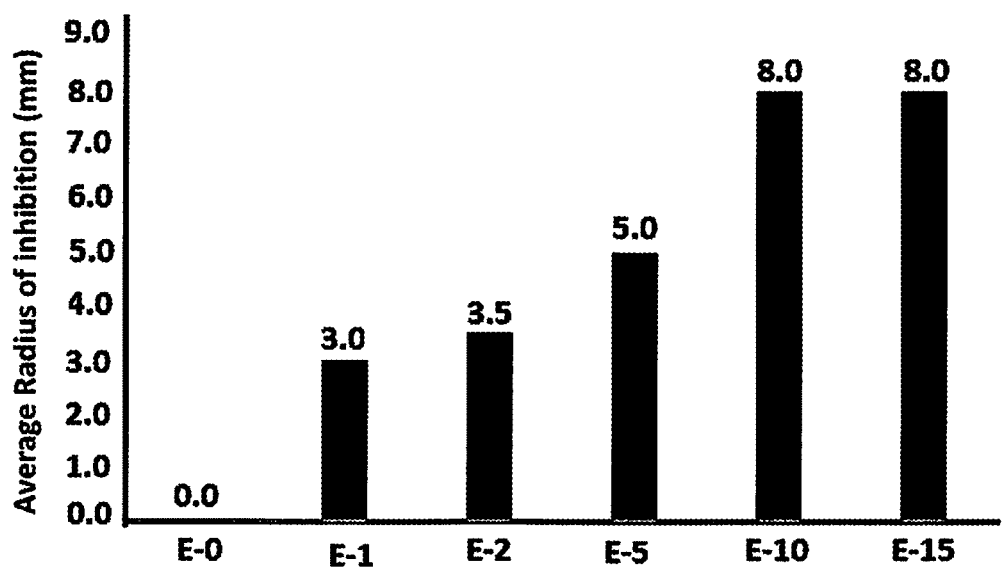
FIG. 7 shows the results of a disc diffusion antibiotic sensitivity test (as radiuses in mm of sterile zones on agar) for the antibacterial activity of emulsifying base ointments (example 1).

FIG. 7 shows a strong correlation between the copper (II) gluconate concentration in the emulsifying base and its antibacterial effect. The minimal recommended concentration of copper (II) gluconate was determined as 1.25% w/w.

Stability Test of Emulsifying Base Ointments Formulations

Measurements that were done after storage are divided into two groups:
"room conditions", referring to measurement of ointment sample, which was stored at room temperature; and
"37° C." referring to measurement of ointment sample, which was stored in the incubator at 37° C.

All Petri dishes that were used for antimicrobial efficacy tests were triplicated for calculating of standard deviation. The samples were stored in a closed container.

Figure 8:
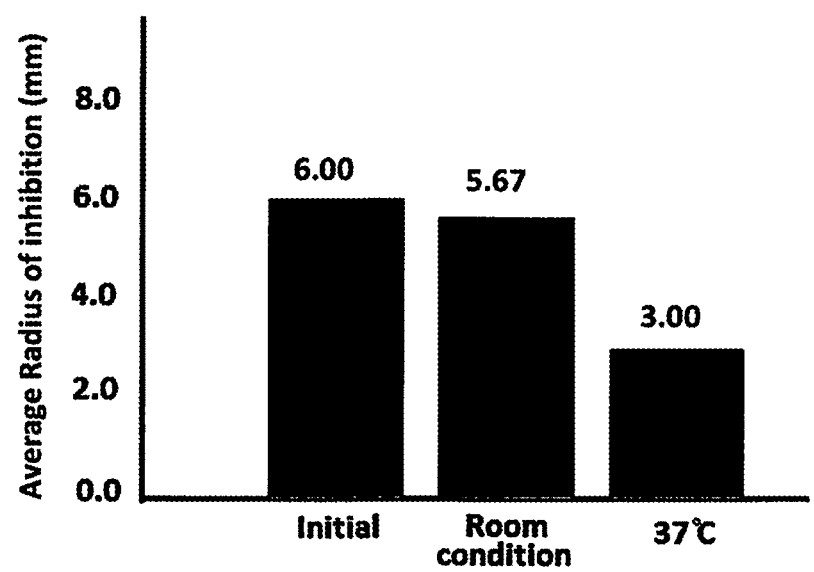
FIG. 8 shows the results of stability test of emulsifying base ointments (example 1) using a disc diffusion antibiotic sensitivity test (as radiuses in mm of sterile zones on agar) at preparation time and after 6 months' storage at room temperature and at 37° C.

FIG. 8 presents inhibition radius of bacterial growth at beginning and in after 6 months of E-5 emulsifying base ointment sample.

Example 2—Absorption Base Ointments that Generate Cu(I) Ions

Preparation

For preparation of 100 gram of absorption base, 35 g of vaseline and 35 g of lanolin were heated in a chemical glass on water bath at 70° C. till melted together into a yellowish transparent liquid and then 30 g of glycerol 80% w.t was added. The mixture was withdrawn from the water bath and cooled by stirring with a spatula until completely congealed.

Ascorbyl palmitate and copper(II) gluconate may be added directly to the prepared base with a mortar and pestle for massive quantities (20-100 g) of ointment and with the help of a clock glass and plastic spatula for a small amount (1-4 g) of ointment. However, for better dispersion of the ascorbyl palmitate and the copper(II) gluconate, they were mixed with glycerol 80% w.t. and then added to the mixture of vaseline and lanolin (1:1 ratio). Metal copper in the powder form was added in amount of 2% w.t. of ointment. Copper(II) gluconate and ascorbyl palmitate were used in 1.4:1 mole ratio (while the stoichiometric ratio is 1:1) because of low stability of ascorbyl palmitate and necessity of prevention of the copper powder oxidation. Four ointments with different mass concentrations of copper(II) gluconate of 10% w.t. (A-10), 11% w.t. (A-11), 13% w.t. (A-13) and 15 w.t. (A-15) were used. Composition of these ointments is presented in Table 7.

TABLE 7

Composition of absorption base ointments that generate Cu(I) ions

| Material | Ointment Amount (% w.t.) | | | |
|---|---|---|---|---|
| | A-10 | A-11 | A-13 | A-15 |
| Vaseline | 24.45 | 23.96 | 22.97 | 21.98 |
| Lanolin | 24.45 | 23.96 | 22.97 | 21.98 |
| Glycerol | 19.56 | 19.16 | 18.37 | 17.58 |
| Copper(II) gluconate | 10.00 | 11.00 | 13.00 | 15.00 |
| Ascorbyl Palmitate | 6.50 | 7.15 | 8.45 | 9.75 |
| Water | 4.89 | 4.79 | 4.59 | 4.40 |
| Copper powder | 2.00 | 2.00 | 2.00 | 2.00 |

Antibacterial Effect

Figure 9:
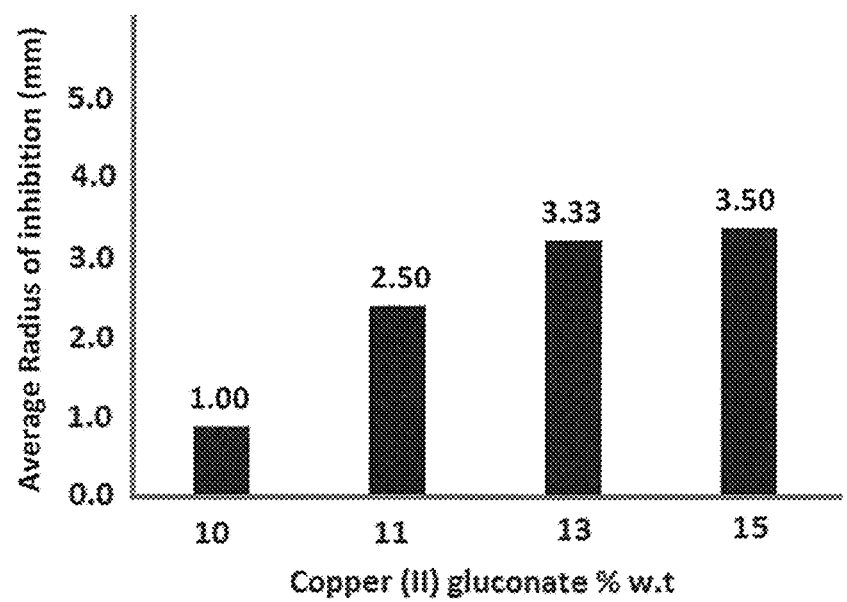
FIG. 9 shows the results of a disc diffusion antibiotic sensitivity test (as radiuses in mm of sterile zones on agar) for the antibacterial activity of absorption base ointments (example 2).

According to FIG. 9, the relation between inhibition radius of bacterial growth and copper (II) gluconate mass concentration is similar to the one in FIG. 7. Again, the more copper (II) gluconate was in the emulsifying base, the inhibition radius was larger. However, in the case of the emulsifying base formulation, a lower Cu(II) concentration is required for inhibition, and therefore it is termed as "quick release" ointment. The absorption base ointment is termed as "slow release" ointment.

Stability Test of Absorption Base Ointments Formulations

Measurements that were done after storage are divided into two groups:

"room conditions", referring to measurement of ointment sample, which was stored at room temperature; and "37° C." referring to measurement of ointment sample, which was stored in the incubator at 37° C.

All Petri dishes that were used for antimicrobial efficacy tests were triplicated for calculating of standard deviation. The samples were stored in a closed container.

Figure 10:
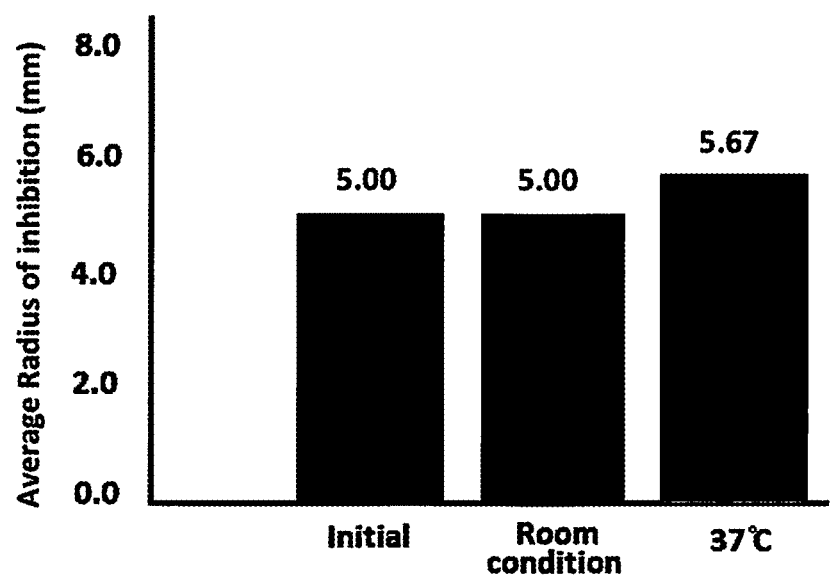
FIG. 10 shows the results of stability test of absorption base ointments (example 2), using a disc diffusion antibiotic sensitivity test (as radiuses in mm of sterile zones on agar) at preparation time and in after 2 months storage at room temperature and at 37° C.

FIG. 10 presents inhibition radius of bacterial growth at beginning and in after 2 months of A-10 absorption base ointment sample.

It will be understood that the invention is described above by way of examples only and modifications may be made whilst remaining within the scope and spirit of the invention.

What is claimed is:

1. An antimicrobial formulation comprising a monovalent copper ions (cuprous, $Cu^{1}+$) generating system, wherein the monovalent copper is produced in situ by reduction of divalent copper ions (cupric, $Cu^{2}+$) selected from copper sulphate, $CuSO_4$, copper chloride, $CuCl_2$, copper acetate, $Cu(CH_3COO)_2$, and copper gluconate, $C_{12}H_{22}CuO_{14}$ in the presence of a reducing agent; wherein the divalent copper ions source is a salt or complex which is able to release divalent copper ions into the reaction mixture that is an aqueous solution; wherein the reducing agent is selected from ascorbic acid or derivatives or salts thereof and metallic copper; wherein, when the reducing agent is metallic copper, the reduction is in the presence of a stabilizing ligand and the metallic copper is in the form of powder, wires, net, sheets or nanoparticles; and wherein the stabilizing ligand is acetonitrile.

2. The antimicrobial formulation according to claim 1, comprising:

ointment comprising copper powder (0.1-5% w/w) as a metallic copper source, copper(II) gluconate (0.1-15%) or copper(II) sulfate (0.1-15%) or any combination thereof as a divalent copper ions source, ascorbyl palmitate (0.1-15%) or ascorbic acid (0.1-15%) or any combination thereof as a reducing agent, and glycerol (0.1-25%), Vaseline (0.1-25%), lanolin (0.1-25%), sodium dodecyl sulfate (SDS) (0.1-2%), talc (0.1-0.5%) and water (0.1-15%) as filling agents.

3. The antimicrobial formulation according to claim 1, comprising:

ointment comprising copper powder (0.1-5% w/w) as a metallic copper source, copper(II) gluconate (0.1-15%) or copper(II) sulfate (0.1-15%) or any combination thereof as a divalent copper ions source, ascorbyl palmitate (0.1-15%) or ascorbic acid (0.1-15%) or any combination thereof as a reducing agent, and stearyl alcohol (0.1-28%), sodium lauryl sulfate (0.1-2%), glycerol (0.1-28%) and Vaseline (0.1-18%), lanolin (0-15%), sodium dodecyl sulfate (SDS) (0.12%), talc (0.1-0.5%) and water (0.11-45%) as filling agents.

4. The antimicrobial formulation according to claim 1, for use as dressings for healing of chronic wounds and burns.

5. The antimicrobial formulation according to claim 1, for use in preventing wound infections.

6. The antimicrobial formulation according to claim 1, for use in preventing infections in implants and medical/surgical devices.

7. The antimicrobial formulation according to claim 1, for use in the treatment of skin infections, such as acne and herpes.

8. The antimicrobial formulation of claim 1, for use in skin healing.

9. A composition comprising the formulation of claim 1, for use as a cosmetic.

10. A bandage comprising the formulation of claim 1, for use in the treatment of anaerobic infections.

11. A bandage according to claim 10, wherein the external side of the bandage is sealed against penetration of oxygen from the external environment.

12. An adhesive bandage comprising:

copper wires; and ointment comprising copper powder (0-5%, w/w), copper(II) gluconate (0.1-15%) or copper (II) sulfate (0.1-15%) or any combination thereof as a divalent copper ions source, ascorbyl palmitate (0.1-15%) or ascorbic acid (0.1-15%) or any combination thereof as a reducing agent, and glycerol (0.1-25%), Vaseline (0.1-20%), lanolin (0.1-15%), sodium dodecyl sulfate (SDS) (0.1-2%), talc (0.1-0.5%) and water (0.1-15%) as filling agents.

* * * * *